United States Patent [19]

Vorys

[11] 4,372,951

[45] Feb. 8, 1983

[54] VAGINAL DELIVERY FOR PHYSIOLOGIC FOLLICULAR-LUTEAL STEROID TREATMENT

[76] Inventor: Nichols Vorys, 1450 Hawthorne Ave., Columbus, Ohio 43203

[21] Appl. No.: 285,590

[22] Filed: Jul. 21, 1981

Related U.S. Application Data

[63] Continuation-in-part of Ser. No. 83,636, Oct. 11, 1979, Pat. No. 4,291,028, which is a continuation of Ser. No. 865,851, Dec. 30, 1977, abandoned.

[51] Int. Cl.³ .............................................. A61K 31/56
[52] U.S. Cl. .................................................... 424/239
[58] Field of Search ................ 424/238, 241, 243, 239

[56] References Cited

U.S. PATENT DOCUMENTS 3,895,103 7/1975 Zeffaroni ............................ 424/238
4,291,014 9/1981 Keith et al. ......................... 424/238

OTHER PUBLICATIONS

Chem. Abstracts vol. 88, 1978, pars. 16, 384f.

Primary Examiner—Elbert L. Roberts
Attorney, Agent, or Firm—Porter, Wright, Morris & Arthur

[57] ABSTRACT

A vaginal delivery system which provides an effective concurrent dosage of combined exogenous estrogenic active steroid and exogenous progestational active steroid during the corpus luteum phase of a follicular-luteal drug administration cycle to provide predictable physiologic levels of such steroids for the finite period of time of the corpus luteum phase of the drug administration cycle.

15 Claims, No Drawings

VAGINAL DELIVERY FOR PHYSIOLOGIC FOLLICULAR-LUTEAL STEROID TREATMENT

This is a continuation-in-part of my application entitled "Follicular Phase Estrogen or Progestin with Physiologic Estrogen/Progestin Luteal Replacement Drug Delivery System", Ser. No. 83,636 filed Oct. 11, 1979, now U.S. Pat. No. 4,291,028, which in turn was a continuation of my application Ser. No. 865,851, filed Dec. 30, 1977 now abandoned. The specification of the said application is incorporated by reference as if herein set out in full.

In the above application, I describe the follicular luteal method of treatment and/or regulation of the menstrual cycle. In brief, the method consists of determining the presenting endogenous estrogen characteristic of the patient and identifying the patient's presenting endogenous estrogen characteristic as one of euestrogenic, hyperestrogenic, or hypoestrogenic. Effective dosages of pharmacologically active sex steroid compositions (selected from the groups of estrogenic active steriod compositions and progestational active steroid compositions) are administered to the patient in an ordered temporal succession in a follicular-luteal design cycle based on the identified endogenous estrogen characteristic and the prevailing clinical objective for gynecological treatment of the patient.

In one example of a follicular-luteal dosage cycle, during the follicular phase of the menstrual cycle there is a first period of absence of administration of any pharmacologically active sex steroid, e.g. during days 1 through 7 of the cycle. There is a following period of administration of an appropriate dose of exogenous estrogenic active or progestational active steroid, for the next 7 days of the cycle, e.g. during days 8 through 14, adapted to the identified endogenous estrogen characteristic of the patient and the presenting clinical objective for gynecological treatment. Thus, in the later half of the follicular phase of the example:

Euestrogenic and hyperstrogenic presenting patients are administered a progestational active steroid during days 8 through 14 of the drug administration cycle, if contraception is desired.

The hypoestrogenic patient is administered an estrogenic active steroid during the second half of the follicular phase, during days 8 through 14, in menstrual dysfunction patients.

Euestrogen and hyperestrogen menstrual dysfunction patients are administered no exogenous estrogen or progestin in the second half of the follicular phase, during days 8 through 14.

Hyperandrogen patients are administered an estrogenic active steroid during days 7 through 14 of the follicular phase when the presenting problem is clinical hyperandrogenism associated with menstrual dysfunction.

During the luteal phase of the menstrual cycle, in all cases, in the example referred to above, there is administered an effective dosage of a pharmacologically active composition which comprises a combination of an estrogenic active steroid and a progestational active steroid. The relative dosages and administration sequences of a combined estrogen dosage and progestin dosage have a physiologic effect on the pituitary gonadotropics and uterine endometrim which is biologically equivalent to the corpus luteum in the normal ovulatory menstrual cycle.

In this manner, separate follicular and luteal phases are established according to a predetermined optimized design cycle and the profile of pharmacological activity of the phase, or a segment thereof, may be manipulated in accordance with a presenting clinical objective based upon the patient's presenting characteristic. Thus, the pharmacological activity of the exogenous sex steroid compositions administered for menstrual dysfunction is analogous to the design objective of a normal ovulating menstrual cycle. In patients with a contraception clinical objective, a sex steroid having progestational activities is administered during the later half of the follicular phase.

In accord with the follicular-luteal method, various tablet administration systems of orally active synthetic estrogenic and progestational active sex steroids are set forth in the above Specification and are claimed in my co-pending application Ser. No. 069,275 filed Aug. 24, 1979, now U.S. Pat. No. 4,292,315 a division of my application Ser. No. 865,851, now abandoned.

The follicular-luteal method provides a temporally based administration of sex steroids which is relatively independent of the potency of the exogenous sex steroid administered, once an effective level of pharmacological activity is achieved to maintain the predetermined temporal correspondence between endogenous levels and the exogenous dosage as determined by the optimized design of the overall cycle and the clinical objective for treatment. The efficacy of follicular-luteal methods appears to result from the biological activity of unopposed estrogenic active steroids or progestational active steroid administered during the separate follicular phase and the combined estrogenic active steroid plus progestational active steroid administered in the separate, following, luteal phase. A predetermined profile of pharmacological activity is provided with respect to the cycle as a whole; and the efficacy of the follicular-luteal method is essentially independent of the relative potency of the particular sex steroid administered, as well as the route of administration.

In accord with the preferred embodiment of the invention which I describe herein, the follicular-luteal method may utilize a "zero order kinetic" exogenous administration of the natural sex steroids, i.e., the estrogen, 17 beta estradiol, and progesterone, in which a regular release of the exogenous steroid composition in a steady state results in a corresponding predictable absorption and metabolism of the drug in the body tissues. In this manner, the delivery of exogenous steroids may be "targeted" to the specific body organ in which it is desired that an intended effect be achieved; other organs such as liver, in which unintended effects may occur, may be bypassed. Thus, the efficient metabolic and therapeutic utilization of an exogenous pharmacological composition administered may be enhanced; and the development of adverse metabolic side effects may be reduced. "Zero order kinetic" drug administration is described inter alia in pending patent applications of Dr. Alec Keith of State College, Penn. and Miami, Fla. Other methods for the controlled timed release of predetermined amounts of pharmacologically active compositions at a "target" site are also known.

Used in connection with the follicular-luteal method, a zero-order kinetic delivery system allows the effective vaginal or transdermal exogenous administration of the "natural" steroids, 17 beta-estradiol and progesterone. In this manner, the enterohepatic circulation of exogenous steroids, and steroid metabolism in the liver which heretofore have been considered the cause of adverse metabolic side effects associated with the administration of exogenous synthetic sex steroids by oral dosage are essentially avoided. Thus, a pharmacological administration system is provided in a design, which mimics the exact secretion rate of "normal" follicular estrogen and combined estrogen and progesterone in the corpus luteum,—which the "normal" ovary itself may physiologically produce in the optimum "normal" cycle. And this follicular-luteal administration will be provided at the organ site where the exogenous steroids are to be utilized. Hence, an efficient route of steroid administration is achieved and the possibility of adverse metabolic effects, which have been associated with the oral delivery of sex steroids may be avoided. In such a delivery system, besides the long known natural estrogen, 17 beta-estradiol and natural progesterone, other synthetic estrogenic active steroids and progestational active steroids may also be exogenously administered.

Thus, a follicular-luteal steroid treatment which utilizes a zero order kinetic drug delivery is provided. In this manner, the physiological advantages incident to the temporally related drug administration of the follicular-luteal method, as set forth in my parent application will be achieved, and the efficiency in pharmacological administration incident to a zero order kinetic delivery system will also be realized. As a result, an effective optimum dosage of exogenous sex steroids will be efficiently delivered to the target organ system; other body systems, such as the liver, in which adverse metabolic side effects have occurred will be bypassed. In addition to this physiological benefit, advantages of convenience in use by the patient are also realized, since, for example, the rigorous discipline of daily tablet administration may not be required in a targeted absorption/release delivery system.

In the preferred embodiment, a standardized corpus luteum for the follicular-luteal method is administered by the controlled membrane release of combined estrogenic active steroid and progestational active steroid by a patient inserted cervical ring or vaginal suppository. Preferably, the duration of the standardized corpus luteum administered by the controlled release insert is 14 days, from day 15 to 28, in a 28 day design cycle, and the patient insert is maintained in the body during the duration of the corpus luteum phase of the cycle.

The vaginal insert will provide a steady state release of exogenous steroids and will produce predictable placed levels of estrogenic active and progestational active sex steroids in the target system during the finite period of time that the insert is maintained in the vagina. Depending upon the type of follicular-luteal system involved, the desired pharmacological activity profile of the exogenous steroids to be delivered in a controlled manner by the vaginal insert is equivalent to the activity obtained by oral dosage, as may be derived in accord with the skill of the art, from the description in the Specifications and Drawings of my above referred to applications. Similarly, the dosage release may also be adjusted to provide effective dosage depending upon the relative potency of the particular steroid compositions administered, as well as to provide the gynecological treatment required by the prevailing clinical objective.

As is known, the physical form of the vaginal insert should be adopted to conform to the physiological environment of the vagina, where, during the corpus luteum phase, the insert will be continuously maintained for the approximately 14 days of the corpus luteum phase (days 15 through 28).

In a follicular-luteal delivery system in which the standardized corpus luteum dosage of exogenous steroids is delivered by means of a vaginal insert, the exogenous steroid administration of the follicular phase may take any known physical form, e.g. tablet, syrup, subcutaneous, suppository, transdermal, membrane delivery, etc.

Thus, a drug delivery system is provided in which the pharmacological activity profile of a design optimum corpus luteum phase may be standardized and the combined estrogenic active and progestational active exogenous sex steroids administered during the luteal phase of the drug administration cycle may be vaginally delivered in a controlled manner by the insert. The insert is maintained within the vagina during the duration of the luteal phase of drug administration. Convenience to the patient results since patient application of the single vaginal insert at the beginning of the luteal phase, and its removal at the onset of menstruation, is the only patient activity required for the 14 day luteal phase. Flexibility in prescribing for a clinical objective is also achieved since the preeceding follicular phase of steroid administration is determined by the presenting state of the patient. The administration of an effective dosage of the required pharmaceutical composition during the follicular phase may take any physical form.

The following are summary examples of delivery systems for use with the follicular-luteal method, each in a 28 day steroid administration cycle:

EXAMPLE I

A hypoestrogen patient in which steroid replacement is provided as treatment for a menopause condition with uterus in situ. The follicular-luteal method provides: (A) in the follicular phase (i) the absence of administration of exogenous sex steroids for the first 7 days; and (ii) the administration of an effective dosage of exogenous estrogenic active steroid for the next 7 days; followed by (B) the standardized corpus luteum phase of 14 days which includes the dosage of an effective amount of combined estrogenic active steroid and progestational active steroid.

EXAMPLE II

The euestrogen, hypoestrogen or hyperestrogen presenting patient who desires contraception will be provided with exogenous progestational active steroid in the later half of the follicular phase of the cycle followed by the standardized corpus luteum.

EXAMPLE III

Those euestrogen or hyperestrogen patients with menstrual dysfunction are treated with a standardized corpus luteum consisting of a combined estrogenic active steroid and progestational active steroid only for the last 14 days of the cycle.

EXAMPLE IV

Hypoestrogen menstrual dysfunction patients are treated with exogenous estrogenic active steroid during days 8 through 14 of the cycle followed by a standardized 14 day corpus luteum of combined estrogenic and progestational active steroids.

EXAMPLE V

Hyperandrogen menstrual dysfunction patients are managed with exogenous estrogenic active steroid during days 8 through 14 followed by the standardized 14 day corpus luteum of combined estrogenic and progestational active steroids.

In the foregoing examples dealing with one type of follicular-luteal method, the same standardized corpus luteum is provided for each presenting clinical state and the objective of gynecological treatment for that state is achieved by variation of the follicular phase of the cycle. The following table summarizes the embodiments of the Examples (E=Estrogenic active steroid), P=Progestational active steroid):

TABLE I

| Example | Follicular Phase (14 Days) | | Luteal Phase (14 Days) |
|---|---|---|---|
| | Days/Drug | Days/Drug | Days/Drug |
| I. | 1–7/none | 8–14/E | 15–28/combined E & P |
| II. | 1–7/none | 8–14/P | 15–28/combined E & P |
| III. | 1–14/none | | 15–28/combined E & P |
| IV. | 1–7/none | 8–14/E | 15–28/combined E & P |
| V. | 1–7/none | 8–14/E | 15–28/combined E & P |

For the Examples herein, and for descriptions of other follicular-luteal pharmacological administration sequences, the potency equivalent of the particular steroid administered, and appropriate cycle phases, for a predetermined pharmacological effect may be determined in accord with the skill of the art following my above referred to parent application, Ser. No. 865,851. For vaginal delivery, the "natural" steroids, 17 beta estradiol and progesterone are preferred.

Table I shows the standardized corpus luteum administration phase of the cycle which may be adapted for vaginal delivery by controlled release of combined estrogenic active steroids and progestational active steroids during the 14 day extent of the corpus luteum phase. The vaginal insert may be in the form of a pliable ring which encompasses the cervix and includes a pharmaceutical carrier/controlled release agent which will deliver the predetermined amount of the combined estrogenic active and progestational active steroid compositions to provide the desired pharmacological activity in accord with the requirements of the luteal phase for the particular follicular-luteal method involved. Preferably, the insert is maintained in the vagina for the extent of the luteal phase of the cycle to provide the delivery of the effective amounts of combined estrogen active steroid and progestin active steroid required in the luteal phase. The physical shape, form, and composition of the vaginal insert and the chemical/biological/pharmaceutical mechanism of the controlled release of the steroids required may be adapted in accordance with known forms and mechanisms for the delivery of pharmaceutical compositions.

A separate vaginal insert or orally administered tablet of synthetic estrogen or progestin may similarly be adapted to the delivery of pharmacologically active sex steroid compositions required during the follicular phase of the cycle. Thus, for example, the temporal relationship of follicular estrogen in hypoestrogenic menstrual dysfunction patients, or follicular progesterone in patients desiring contraception, may be obtained by synthetic oral or transdermal natural estrogen or progesterone or vaginal suppositories of the natural sex steroids in a delivery media which is programmed to last from follicular days 8 through 14. A package of the complete delivery system will thus include the luteal vaginal insert and the follicular delivery system, if the separate follicular and luteal dosages are administered by separate delivery systems. Application instructions will also be provided. The vaginal insert will include means for the controlled release of pharmacologically active estrogenic and progestational active sex steroids in accord with the corpus luteum phase of the cycle, thus including the requisite follicular and luteal administration of estrogen and progesterone dosage required in a single insert. Or two inserts, each characterized with one of estrogenic activity or progestational activity may be provided and inserted in a temporal sequence to provide the proper follicular dosage followed by a proper estrogen and progesterone luteal phase for a particular treatment. In this system a cervical ring device or vaginal suppository releases predictable amounts of the active sex steroid for the programmed period of time of the optimal corpus luteum phase of the cycle, and mimics the natural secretion rate of the natural hormones, 17 beta estradiol and progesterone produced by the ovary's corpus luteum.

The availability of a hypolymer zero order kinetic delivery system in conjunction with the vaginally inserted medium makes it possible to use 17 beta estradiol and natural progesterone, combined in the standardized corpus luteum phase, rather than "synthetic" sex steroids. If these "natural" sex steroids, 17 beta estradiol and progesterone, where to be administered exogenously by oral dosage, they would be absorbed by the gastro-intestinal tract and metabolized so rapidly, as to become relatively ineffective. Accordingly, despite the long knowledge in the art of these natural sex steroids, the synthetic estrogens and progestins were substituted for natural harmones in oral delivery systems. With the use of these synthetic steroids certain metabolic problems have resulted with oral administration of combined estrogen and progestins. The preferred zero order kinetic vaginal delivery system of this application avoids the gastro intestinal tract enzymes, minimizes exogenous estrogen exposure to the liver, eliminates the extended enterohepatic recirculation and cholystasis of synthetic estrogens, and provides sex steroid target organ blood and tissue levels that are analogous to the normal ovulatory menstrual cycle.

Accordingly, the vaginal corpus luteum delivery system allows the use of natural estrogen and progesterone at a physiologic secretion rate and by a route of administration that avoids estrogen overdose. The delivery system achieves these salutary effects and also provides greatly enhanced convenience to the patient. Further by delivering the luteal phase of the cycle separately great flexibility is obtained in managing the second half of the follicular phase with either oral synthetic, or transdermal or vaginal natural estrogen or progesterone depending on the therapeutic indication, and personal esthetic and practical preference of the patient.

What I claim is the following:

1. A method of regulation of the menstrual cycle in which effective dosages of pharmacologically active steroid compositions selected from the group of estrogenic active steroids and progestational active steroids are administered in a temporal succession in a correspondence with a first follicular phase and a following luteal phase in an approximately 28 day menstrual cycle, in which, dosage of the follicular phase is dependent upon the presenting endogenous estrogen characteristic of the patient, and the luteal phase includes:

a vaginal delivery system which provides effective concurrent dosages of (1) a pharmacologically active steroid selected from the group of estrogen active steroids and (2) a pharmacologically active steroid selected from the group of progestational active steroids, administered together, for a finite period of time of approximately 14 days during the luteal phase of the drug administration cycle, whereby predictable physiologic levels of activity of each steroid administered are provided during the luteal phase of the drug administration cycle.

2. The follicular-luteal method in accord with claim 1 in which the concurrent vaginal delivery of an estrogen active steroid with a progestational active steroid during the luteal phase provides a standardized level of pharmacological activity which mimics the physiological activity of an optimum predetermined normal menstrual cycle.

3. The method of claim 2 in which the standardized level of steroid activity provided in a system is a level of activity which is the same for euestrogen, hyperestrogen and hypoestrogen presenting endogenous estrogen conditions.

4. The system of claim 1 or claim 2 or claim 3 for treatment of a menstrual dysfunction condition in a patient of one of an (1) euestrogen and (2) hyperestrogen presenting condition.

5. A delivery system in accord with claim 1 or claim 2 or claim 3 which provides by vaginal delivery an effective dosage, related to the presenting endogenous estrogen characteristic of the patient, of one of (1) an estrogenic active steroid and (2) a progestational active steroid, during the later portion of the follicular phase of the drug administration cycle, preceding the administration of steroids in the luteal phase of the drug administration cycle.

6. A vaginal delivery system for providing pharmacologically active exogenous steroids with respect to a predetermined first follicular phase and a following luteal phase according to a temporal relationship in a single menstrual cycle having a duration of approximately 28 days in which a first steroid, having one of (1) estrogenic activity and (2) progestational activity, is administered, beginning with the later part of the follicular phase, for a period of about 21 days during the menstrual cycle; and for the last approximately 14 days of the 21 day administration of the first steroid, a second steroid, having the other of (1) estrogenic activity and (2) progestational activity, is concurrently administered therewith during the luteal phase.

7. The system of claim 6 in which the presenting endogenous estrogen state of the patient is one of euestrogenic and hyperestrogenic and the first steroid administered is a progestational active steroid.

8. The system of claim 6 in which the presenting endogenous estrogen state of the patient is hypoestrogenic and the first steroid administered is an estrogenic active steroid.

9. The system of claim 8 for treatment of a menopause condition.

10. The system of claim 7 for contraception.

11. The system of claim 8 for contraception.

12. A follicular-luteal method in accord with claim 1 or claim 2 or claim 3 in which a pharmacologically active steroid composition related to the presenting endogenous estrogen characteristic of the patient is one of (1) an estrogenic active steroid and (2) a progestational active steroid administered by means other than vaginal delivery.

13. The delivery system of claim 1 or claim 6 in which the steroid having an estrogenic activity is 17 beta estradiol.

14. The delivery system of claim 1 or claim 6 in which the steroid having a progestational activity is progesterone.

15. The delivery system of claim 1 or claim 6 in which the steroid having an estrogenic activity is 17 beta estradiol and the steroid having a progestational activity is progesterone.

* * * * *